United States Patent
Weber

(10) Patent No.: US 9,249,247 B2
(45) Date of Patent: *Feb. 2, 2016

(54) ACRYLIC POLYMER

(75) Inventor: Dirk Weber, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 439 days.

This patent is subject to a terminal disclaimer.

(21) Appl. No.: 13/503,750

(22) PCT Filed: Nov. 15, 2010

(86) PCT No.: PCT/EP2010/067451
§ 371 (c)(1),
(2), (4) Date: Jun. 30, 2012

(87) PCT Pub. No.: WO2011/058163
PCT Pub. Date: May 19, 2011

(65) Prior Publication Data
US 2012/0258066 A1 Oct. 11, 2012

(30) Foreign Application Priority Data
Nov. 19, 2009 (EP) .................................. 09176065

(51) Int. Cl.
*A61K 8/81* (2006.01)
*C08F 220/18* (2006.01)
*A61Q 5/06* (2006.01)
*C08F 220/06* (2006.01)

(52) U.S. Cl.
CPC ............ *C08F 220/18* (2013.01); *A61K 8/8152* (2013.01); *A61Q 5/06* (2013.01); *C08F 220/06* (2013.01); *C08F 2220/1816* (2013.01)

(58) Field of Classification Search
None
See application file for complete search history.

(56) References Cited

U.S. PATENT DOCUMENTS

2010/0135918 A1* 6/2010 Kim et al. ...................... 424/47

FOREIGN PATENT DOCUMENTS

GB 1312098 4/1973

OTHER PUBLICATIONS

International Search Report for PCT/EP2010/067451 mailed Dec. 10, 2010.
Written Opinion of the International Searching Authority mailed Dec. 10, 2010.
San Esters Corporation, Industrial & Specialty Monomers, http://www.sanesters.com/download/SAN%20ESTERS%20BROCHURE.pdf (2015).
BASF Technical Information, Methacrylic Acid, technical, TI/ED 1574e, May 2014.
BASF Technical Data Sheet, Ethyl Acrylate, Aug. 2003.

* cited by examiner

*Primary Examiner* — Hasan Ahmed
(74) *Attorney, Agent, or Firm* — Nixon & Vanderhye P.C.

(57) ABSTRACT

The present invention relates to acrylic emulsion polymers having excellent hair styling properties as well as their use in hair care preparations in particular hair styling preparations.

14 Claims, No Drawings

ACRYLIC POLYMER

This application is the U.S. national phase of International Application No. PCT/EP2010/067451 filed 15 Nov. 2010 which designated the U.S. and claims priority to EP 09176065.2 filed 16 Nov. 2009, the entire contents of each of which are hereby incorporated by reference.

The present invention relates to acrylic emulsion polymers having excellent hair styling properties as well as their use in hair care preparations in particular hair styling preparations.

Acrylate Copolymers such as e.g. Luvimer® (BASF), Balance® (Akzo Nobel) or Acudyne®(Rohm and Haas) are widely used in the Hair Care Industry as setting polymers for Aerosol and non-Aerosol Sprays. These polymers are prepared with emulsion polymerization technology which allows a good control over critical polymer parameters like molecular weight, particle size in the nm range and residual monomer content. However, there is an ongoing need for an economically attractive method of preparation of acrylic emulsion polymers for cosmetic compositions, in particular hair care preparations which have a specifically low residual monomer content without the characteristic off odours resulting from residual monomers.

In addition the acrylic emulsion polymers should be readily formulated into cosmetic compositions such as in particular into hair care preparations in solvents or solvent mixtures with an increased water fraction. The preparations should have better sprayability coupled with good mechanical properties of the films formed. Besides the good compatibility with the customary cosmetic ingredients the acrylic emulsion polymers should provide the hair with good setting and prolonged hold, have good wash-out properties and permit formulation as optically clear VOC-55 aerosols (i.e. with a VOC content of at most 55% by weight). In addition, the treated hair should have good haptic properties such as, for example, a good feel to the touch and being non-sticky.

Surprisingly, it has been found that acrylic emulsion polymers obtainable from emulsion polymerisation of methacrylic acid, n-butyl methacrylate and ethylacrylate have a low residual monomer content while exhibiting excellent hair styling properties as outlined above.

Thus, the invention relates in a first embodiment to a process for the preparation of acrylic emulsion polymers comprising subjecting a monomer composition consisting of a mixture of methacrylic acid (MAA), n-butyl methacrylate (BMA), ethylacrylate (EA) and ethyl methacrylate (EMA) to emulsion polymerization.

In a particular embodiment the monomer composition consists of a mixture of 10-30 wt.-% of methacrylic acid, 35-65 wt.-% of n-butyl methacrylate, 5-15 wt.-% of ethyl acrylate and 10-35 wt-% of ethyl methacrylate such as in particular of 15-25 wt.-% of methacrylic acid, 38-60 wt.-% of n-butyl methacrylate, 8-15 wt.-% of ethyl acrylate and 15-25 wt.-% of ethyl methacrylate such as even more in particular of 17-22 wt.-% of methacrylic acid, 44-56 wt.-% of n-butyl methacrylate, 9-15 wt.-% of ethyl acrylate and 15-25 wt.-% of ethyl methacrylate.

Particular good hair styling properties such as excellent high humidity curl retention are obtained when the monomer mixture consists of 15-22 wt.-% of methacrylic acid, 44-56 wt.-% of n-butyl methacrylate, 9-15 wt.-% of ethyl acrylate and 18-22 wt.-% of ethyl methacrylate.

The term 'consisting of' as used according to the present invention means that the total amount of monomer ideally sum up to 100 wt.-%. It is however not excluded that small amount of impurities or additives may be present such as e.g. in amounts of less than 5 wt.-%, preferably less than 3 wt.-% which are e.g. introduced via the respective raw materials.

Preferably the ratio of ethyl methacrylate (EMA) to ethyl acrylate (EA) (w/w) in the monomer compositions indicated above is selected in the range of 4:1 to 1:1, preferably in the range of 2:1 to 1:1, in particular in the range of 2:1 to 1.3:1, which can also be expressed as coefficient of EMA/EA which accordingly should preferably be selected in the range of 4 to 1, preferably in the range of 2 to 1 such as in particular in the range of about 2.0 to 1.3.

It is further preferred that the amount of methacrylic acid used in the monomer compositions is less than 25 wt.-%, such as about 15 to 20 wt.-% and in particular about 20 wt.-% based on the total amount of the monomers in order to further reduce the residual monomer content.

Particular preferred are monomer mixtures wherein the MAA content is about 15-20 wt.-% and the coefficient of EMA/EA is selected in the range of about 2.0 to 1.3.

In another embodiment, the invention relates to acrylic emulsion polymers obtainable by the process according to the invention.

The acrylic emulsion polymers according to the invention are prepared by emulsion polymerization methods according to known methods as outlined below and illustrated in the examples.

The method of free-radically initiated aqueous emulsion polymerization has been described previously on many occasions and is therefore sufficiently known to the person skilled in the art [cf. e.g. Encyclopedia of Polymer Science and Engineering, Vol. 8, pages 659 to 677, John Wiley & Sons, Inc., 1987; D. C. Blackley, Emulsion Polymerization, pages 155 to 465, Applied Science Publishers, Ltd., Essex, 1975; D. C. Blackley, Polymer Latices, 2.sup.nd Edition, Vol. 1, pages 33 to 415, Chapman & Hall, 1997; H. Warson, The Applications of Synthetic Resin Emulsions, pages 49 to 244, Ernest Benn, Ltd., London, 1972; D. Diederich, Chemie in unserer Zeit [Chemistry of our Time] 1990, 24, pages 135 to 142, Verlag Chemie, Weinheim; J. Piirma, Emulsion Polymerization, pages 1 to 287, Academic Press, 1982; F. Holscher, Dispersionen synthetischer Hochpolymerer [Dispersions of Synthetic High Polymers], pages 1 to 160, Springer-Verlag, Berlin, 1969 and DE-A 40 03422]. The free-radically initiated aqueous emulsion polymerization is usually carried out by dispersely distributing the monomers, usually with co-use of dispersants, in the aqueous medium, and polymerizing using at least one free-radical polymerization initiator.

Suitable free-radical polymerization initiators for the free-radical aqueous emulsion polymerization according to the invention are all those which are able to trigger a free-radical aqueous emulsion polymerization. These may in principle be either peroxides or azo compounds. Redox initiator systems are of course also suitable. Peroxides which may be used are, in principle, inorganic peroxides, such as hydrogen peroxide or peroxodisulfates, such as the mono- or di-alkali metal or ammonium salts of peroxide disulfuric acid, for example, its mono- and di-sodium, -potassium or ammonium salts or organic peroxides, such as alkyl hydroperoxides, for example tert-butyl, p-menthyl or cumyl hydroperoxide, tert-butyl perpivalate, and dialkyl or diaryl peroxides, such as di-tert-butyl or di-cumyl peroxide, 2,5-dimethyl-2,5-di(t)butyl-peroxy (hexane) or dibenzoyl peroxide.

The azo compounds used are essentially 2,2'-azobis(isobutyronitrile), 2,2'-azobis(2,4-dimethylvaleronitrile) and 2,2'-azobis(amidinopropyl)dihydrochloride (AIBA, corresponds to V-50™ from Wako Chemicals), 1,1'-azobis(1-cyclohexanecarbonitrile), 2,2'-azobis(2-amidinopropane) salts, 4,4'-azobis(4-cyanovaleric acid) or 2-(carbamoylazo)isobutyronitrile. Suitable oxidizing agents for redox initiator systems are essentially the above-mentioned peroxides. Corresponding reducing agents which may be used are sulfur compounds with a low oxidation state, such as alkali metal sulfites, for example potassium and/or sodium sulfite, alkali metal hydrogensulfites, for example potassium and/or sodium hydrogen sulfite, alkali metal metabisulfites, for example potassium and/or sodium metabisulfite, formaldehyde sulfoxylates, for example potassium and/or sodium formaldehyde sulfoxylate, alkali metal salts, specifically potassium and/or sodium salts, of aliphatic sulfinic acids and alkali metal hydrogen sulfides, such as, for example, potassium and/or sodium hydrogen sulfide, salts of polyvalent metals, such as iron(II) sulfate, iron(II) ammonium sulfate, iron(II) phosphate, enediols, such as dihydroxymaleic acid, benzoin and/or ascorbic acid, and reducing saccharides, such as sorbose, glucose, fructose and/or dihydroxyacetone.

The initiators are usually used in amounts up to 10% by weight, preferably 0.02 to 5% by weight, based on the monomers to be polymerized.

Surfactants can be utilised in order to assist the dispersion of the polymer in water. Suitable surfactants include but are not limited to conventional anionic and/or non-ionic surfactants and mixtures thereof such as Na, K and $NH_4$ salts of dialkylsulphosuccinates, Na, K and $NH_4$ salts of sulphated oils, Na, K and $NH_4$ salts of alkyl sulphonic acids, Na, K and $NH_4$ alkyl sulphates, alkali metal salts of sulphonic acids; fatty alcohols, ethoxylated fatty acids and/or fatty amides, and Na, K and $NH_4$ salts of fatty acids such as Na stearate and Na oleate. Other anionic surfactants include alkyl or (alk)aryl groups linked to sulphonic acid groups, sulphuric acid half ester groups (linked in turn to polyglycol ether groups), phosphonic acid groups, phosphoric acid analogues and phosphates or carboxylic acid groups. Non-ionic surfactants include polyglycol ether compounds and preferably polyethylene oxide compounds as disclosed in "Non-Ionic Surfactants—Physical Chemistry" edited by M. J. Schick, M. Decker 1987. The amount of surfactant used is preferably 0 to 15 wt.-% by, more preferably 0 to 8 wt-%, still more preferably 0 to 5% wt.-%, especially 0.1 to 3 wt-% and most especially 0.3 to 2 wt-% on the total weight of vinyl monomers required.

Chain transfer agent may be added to control the molecular weight. Suitable chain transfer agents include mercaptans such as n-dodecylmercaptan, n-octylmercaptan, t-dodecylmercaptan, mercaptoethanol, iso-octyl thioglycolate, $C_2$ to $C_8$ mercapto carboxylic acids and esters thereof such as 3-mercaptopropionic acid and 2-mercaptopropionic acid. Mixtures of two or more regulators may also be used.

Preferably 0.05 to 5 wt-%, more preferably 0.1 to 3 wt-% and most preferably 0.1 to 1 wt-% of chain transfer agent based on the weight of vinyl monomers required is used. The alkanethiols are usually added to the polymerization together with the monomers.

If, in the polymerization, thiols are used, a subsequent hydrogen peroxide treatment could be required in order to obtain polymers with a neutral odor.

The emulsion polymerization usually takes place with the exclusion of oxygen, for example under a nitrogen or argon atmosphere, at temperatures in the range from 20 to 200° C. Polymerization temperatures in the range from 50 to 130° C., in particular 70 to 95° C. are advantageous.

The polymerization can be carried out batch-wise, semi-continuously or continuously. The polymerization and the monomer and regulator feed are often carried out semi-continuously by the feed method. Preferably, at least some of the monomers, initiators and, if appropriate, regulators are metered into the reaction vessel uniformly throughout the polymerization. However, it is also possible to have an initial charge of the monomers and the initiator in the reactor and to polymerize them, with cooling if appropriate. Another option is to carry out the polymerization using a seed latex prepared from the polymers to be polymerized in the first polymerization phase. The remainder of the monomer mixture is added, preferably by the feed method.

The polymerization reaction advantageously takes place until the monomer conversion is >95% by weight, preferably >98% by weight or >99% by weight.

It is often useful if the aqueous polymer dispersion obtained is subjected to an after-polymerization step in order to reduce further the amount of unreacted monomer. This measure is known to the person skilled in the art (for example EP-B 3957, EP-B 28348, EP-B 563726, EP-A 764699, EP-A 767180, DE-A 3718520, DE-A 3834734, DE-A4232194, DE-A 19529599, DE-A 19741187, DE-A 19839199, DE-A 19840586, WO 95/33775 or U.S. Pat. No. 4,529,753). It is of course also possible to subject the aqueous polymer dispersion obtained to an inert-gas and/or steam stripping, likewise known to the person skilled in the art, before or after the after-polymerization step. This stripping operation preferably takes place after the after-polymerization step. As is described in EP-A 805169, partial neutralization of the dispersion to a pH in the range from 5 to 7, preferably to a pH in the range from 5.5 to 6.5, is advantageous before the physical deodorization.

According to a preferred embodiment of the invention and due to the low monomer content after preparation these possible additional steps can be omitted and the dispersions can be further used as such providing an economical advantage.

The dispersion obtained from emulsion polymerization can either be incorporated directly into an aqueous, aqueous-alcoholic or alcoholic cosmetic preparation, for example a hair-styling preparation, or drying of the dispersion takes place, e.g. spray-drying or freeze-drying, so that the acrylic emulsion polymer can be used and processed in the form of powder.

The polymers are usually partially or completely neutralized, expediently to 5 to 100%, or often to 30 to 95%, using an alkali metal hydroxide or preferably using an amine. In a preferred embodiment, the polymers are partially neutralized, and in a particularly preferred embodiment completely neutralized.

The neutralization is advantageously carried out with a mono-, di- or trialkanolamine having 2 to 5 carbon atoms in the alkanol radical, which is present in etherified form if appropriate, for example mono-, di- and triethanolamine, mono-, di- and tri-n-propanolamine, mono-, di- and triisopropanolamine, 2-amino-2-methylpropanol and di(2-methoxyethyl)amine, an alkanediolamine having 2 to 5 carbon atoms, for example 2-amino-2-methylpropane-1,3-diol and 2-amino-2-ethylpropane-1,3-diol, or a primary, secondary or tertiary alkylamine having a total of 5 to 10 carbon atoms, for example N,N-diethylpropylamine or 3-diethylamino-1-propylamine.

Good neutralization results are often obtained with 2-amino-2-methylpropanol, triiso-propanolamine, 2-amino-2-ethylpropane-1,3-diol or 3-diethylamino-1-propylamine.

Suitable alkali metal hydroxides for the neutralization are primarily sodium hydroxide, or potassium hydroxide and ammonium hydroxide.

Also suitable for the neutralization are aqueous buffer solutions, such as, for example, buffers based on alkali metal or ammonium carbonate or bicarbonate.

The neutralizing agents are preferably added in the form of a dilute aqueous solution to the polymer dispersion.

The pH can, if appropriate, also be adjusted by adding a buffer solution, preference being given to buffers based on alkali metal or ammonium carbonate or hydrogen carbonate.

The polymer solids content of the aqueous polymer dispersions accessible according to the invention is frequently 5 to 70% by weight, often 20 to 60% by weight, or 30 to 60% by weight.

In particular, the acrylic emulsion polymers according to the invention have a molecular weight between 30-500 kDalton, more preferably 50-250 kD and most preferred between 75 and 200 kDalton, and a glass transition temperature between 40 and 140° C., more preferably between 55 and 130° C. and most preferred between 70-120° C. Due to high Tg of the acrylic emulsion polymers no anti-caking agent is needed to prevent the polymers from sticking during storage even at elevated temperature if provided in powder form.

The glass transition temperature $T_g$ is the limit at which, according to G. Kanig (Kolloid-Zeitschrift & Zeitschrift fur Polymere, Vol. 190, page 1, equation 1) the polymer changes from a glassy, brittle state to a rubbery state. Tg values of polymers may e.g. be determined experimentally using techniques such as differential scanning calorimetry DSC.

After neutralization e.g. with 2-amino-2-methylpropanol (AMP), the acrylic emulsion polymers according to the invention are excellent soluble in water, in ethanol and in mixtures of both making them suitable for a wide range of applications and allow the formulation of cosmetic compositions such as in particular hair styling preparations with an increased water content.

Furthermore, the acrylic emulsion polymers according to the invention exhibit a good compatibility with cosmetic ingredients making them especially suitable for cosmetic applications such as in particular hair care applications.

Thus, the invention in a further embodiment relates to cosmetic compositions comprising acrylic emulsion polymers according to the invention and a cosmetically acceptable carrier. The term "cosmetic composition" as used herein refers in particular to cosmetic compositions that can be topically applied to mammalian keratinous tissue such as e.g. human skin or scalp.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), 4$^{th}$ edition, 1992.

The term cosmetically acceptable carrier refers to all carriers and/or excipients and/or diluents conventionally used in cosmetic compositions.

The amount of the acrylic emulsion polymers according to the present invention in the cosmetic compositions, in particular in the hair care preparations according to the invention may easily be chosen by a person skilled in the art in an amount suitable for the desired application. Preferably, a concentration of 0.01-20 wt. %, most preferred of 0.05-10 wt. % based on the total weight of the cosmetic composition is used.

The acrylic emulsion polymers according to the invention furthermore show excellent hair styling properties such as e.g. excellent high humidity curl retention. Thus, the acrylic emulsion polymers according to the invention are in particular suitable for hair styling applications. Due to their excellent water solubility it is further possible to formulate hair styling preparations with an increased water content such as VOC-55 (i.e. with a VOC content of at most 55% by weight) or even no VOC preparations Thus, particular preference is given to the use of the acrylic emulsion polymers according to the invention in hair care preparations. Hair care preparations which may be mentioned are hair treatments, hair lotions, hair rinses, hair emulsions, end fluids, neutralizing agents for permanent waves, hot-oil treatment preparations, conditioners, curl relaxers, styling wrap lotions, setting lotions, shampoos, hair waxes, pomades, hair mousses, hair colorants or hairsprays. Particular preference is given to the use of the acrylic emulsion polymers in hairstyling preparations which are in the form of spray preparations and/or hair mousses.

The acrylic emulsion polymers according to the invention are characterized in hair care preparations by their good compatibility with the nonpolar propellants in spray preparations, in particular with hydrocarbons such as n-propane, isopropane, n-butane, isobutane, n-pentane and mixtures thereof and in particular by the excellent sprayability as pump spray or aerosol.

They are also very readily compatible with other additives customary in hair cares, have a good hair-setting action, form films with very good mechanical properties and are characterized in that they cause virtually no sticking-together of the hair.

Besides the freedom from odor, the acrylic emulsion polymers have excellent results for the application properties in hair care preparations. They dissolve in alcohols such as ethanol or isopropanol and in mixtures of these alcohols with water to form clear solutions. The clarity of the solutions is also obtained when the solutions are used in standard spray formulations together with propellants such as dimethyl ether. In particular, they can be formulated in aqueous low-VOC preparations with at most 55% by weight of volatile organic constituents (VOC-55) to give clear mixtures.

The hair-styling preparations according to the invention can be washed out of the hair without problems. Hair treated therewith has increased softness and a pleasant natural feel. The setting action is also good, making it possible, in principle, to reduce the required amount of film former in the hairspray formulation.

Thus, in a particular embodiment the present invention relates to hair care preparations such as in particular hair styling preparations e.g. aqueous hair styling preparations comprising the acrylic emulsion polymers according to the invention.

The amount of the acrylic emulsion polymers according to the present invention in to hair care preparations such as in particular hair styling preparations is preferably selected within a concentration range of 0.01-20 wt.-%, more preferably within a concentration range of 0.1-10 wt. % such as in particular within a concentration range of 1 to 10 wt.-% based on the total weight of the hair care preparation.

The hair care preparations according to the present invention may be in the form of a (aerosol) spray, (aerosol) foam, gel, gel spray, cream, lotion, liquid or a wax. Hair sprays comprise as well aerosol sprays as pump sprays without propellant. Hair foams comprise as well aerosol foams as pump foams without propellant. Hair sprays and hair foams comprise mainly or exclusively water soluble or water dispersible components. If the components used in hair sprays or hair foams according to the invention are water dispersible, then they may be in the form of micro dispersions with particle sizes of usually 1-350 nm, preferably 1-250 nm. The solid content of such preparations is typically in the range of 0.5 to 20 wt. % of the total weight of the preparation. Such micro dispersions normally do not need further emulsifiers or tensides for their stabilization. In particular the hair styling preparations according to the invention are in the form of styling creams, styling gels, liquid hair-setting preparations, hair foams or hairsprays.

The hair care preparations such as in particular the hair styling preparations may also contain other hair fixative resins, neutralizers, surfactants, solvents, propellants, other preservatives, thickeners, UV-filters and other additives usually employed in such preparations.

Other hair fixative resins may optionally be added to the hair care preparations to provide other properties which may be desired by the formulator, such as a "stiffer" hold of the hair. The other hair fixative resins may be soluble or insoluble in the hair styling preparation. The other hair fixative resins may be present in the hair styling preparation at a concentration of from 0.5 to 6.0 wt.-%, preferably from 1.0 to 3.0 wt.-%, based on the total weight of the hair styling preparation.

The other hair fixative resins which are suitable in the hair care preparation include for example butyl acrylate/ethyl acrylate/methacrylic acid copolymers; polyvinyl pyrrolidone, vinyl pyrrolidone/vinyl acetate compolymers; octylacrylamide/acrylates/butyl-aminoethylmeth-acrylate copolymers; vinylcaprolactam/vinylpyrrolidone/dimethylaminoethylmethacrylate copolymers; methacryloyl ethylbetaine/methacrylate copolymers; methacrylic acid/methacrylic ester copolymer; methacrylic acid/acrylic acid ester copolymers, alkylester of the copolymer of vinyl methyl ether and maleic anhydride; hydroxyethylcellulose quaternized with diallyl dimethyl ammonium chloride, quaternized vinyl pyrrolidone/dimethylaminoethylmethacrylate copolymer, or combinations thereof.

Neutralizers are preferably present in the hair care preparation when the hair fixative resins contain acidic groups, such as carboxylic acid groups, to promote solubility of the resin in the aqueous hair styling composition. For example, the acrylic hair fixative resin is preferably fully neutralized.

Bases which will neutralize the hair fixative resins include for example amines, alkali or alkaline earth metal hydroxides, ammonium hydroxide or combinations thereof. Suitable amine neutralizers include for example 2-amino-2-methyl propanediol, 2-amino 2-methyl propanol, N,N dimethyl 2-amino 2-methyl 1-propanol, mono-isopropanolamine, tri-isopropanolamine, ethanolamine, triethanolamine, morpholine or combinations thereof. Suitable alkali or alkaline earth metal hydroxides include for example sodium hydroxide potassium hydroxide, or combinations thereof. Preferably, the neutralizer is selected from the group consisting of 2-amino 2-methyl propanediol, 2-amino-2-methyl propanol, N,N dimethyl 2-amino 2-methyl propanol, potassium hydroxide, triethanolamine, triisopropanolamine, or combinations thereof.

The amount of neutralizer added to the hair care preparation is preferably that amount to provide solubility of the hair fixative resin in the hair styling composition. Preferably, in a hair styling preparation containing 35 weight percent or less VOC, from 40 to 100 mole percent of the acid groups on the hair fixative resin are neutralized. For a VOC hair styling composition containing greater than 35 weight percent VOC, preferably greater than 50 mole percent of the acid groups on the hair fixative resin are neutralized.

One or more surfactants may be added to the hair care preparation. When surfactants are present in the hair care preparation, they are preferably present at a concentration of from 0.001 to 1.0 weight percent, based on the total weight of the composition. The surfactants which may be used in the hair care preparation include for example anionic, cationic, nonionic, or amphoteric surfactants. For example, suitable surfactants include PPG 28 Buteth 35, PEG 75 lanolin, perfluoropolymethyl isopropyl ether, octoxynol-9, PEG-25 hydrogenated castor oil, polyethylene terephthalate, polyethylene glycol 25 glyceryl trioleate, oleth-3 phosphate, PPG-5-ceteth-10 phosphate, PEG-20 methyl glucose ether, glycereth-7-triacetate, glycereth-7-benzoate, fatty acid ester of polysorbate (TWEEN), or n-alkyl substituted lactam such as n-octyl pyrrolidone, or combinations thereof.

One or more siloxane derivatives may be present in the hair care formulation. When they are used, they are preferably present in a concentration from 0.001 to 1.0 weight percent, based on the total weight of the composition. The siloxane derivatives include for example dimethicones, phenyl trimethicones, dimethiconols, amodimethicones, alkoxylated dimethicones e.g. PEG-12 dimethicone or methoxy PEG/PPG-7/3 aminopropyl dimethicone.

One or more solvents may be added to the hair care preparation of the present invention. The solvents may or may not be VOC. When solvents are added to the hair care preparation they preferably comprise 55 weight percent or less, and more preferably 100 weight percent or less, based on the total weight of the hair care preparation. Suitable solvents include for example $C_1$ to $C_{12}$ straight or branched chain alcohols such as methanol, ethanol, isopropanol, or propanol or combinations thereof.

In a hair care preparation using an aerosol spray, one or more propellants are used. The propellants may or may not be VOC. Preferably, the propellants are used at a total concentration of from 10 to 70 wt.-%; and more preferably from 30 to 60 wt.-% based on the total weight of the hair care preparation. Propellants include for example n-butane, isobutane, dimethyl ether; dimethoxymethane, difluoroethane, chlorodifluoroethane, chlorodifluoromethane, other chlorofluorocarbons or combinations thereof. Preferred propellants are dimethyl ether, 1,1-difluoroethane, n-butane, isobutane or combinations thereof. These propellants are commercially available.

As stated previously, the total VOC in the hair care preparation, whether the VOC is a solvent or propellant, should be 70 wt.-% or less based on the total weight of the hair care preparation.

Other preservatives which may be used in the hair care preparation include for example isothiazolones, benzyl alcohol, or imidazolidinylurea. The other preservatives are preferably used in an amount of about 0.001 to 1.0 wt.-% based on the total weight of the hair care preparation.

One or more thickeners may be desirable in a hair care preparation which is applied to the hair in form of a mousse or styling gel. Suitable thickeners include for example polycarboxylic acid thickeners such as acrylates/steareth-20 methacrylate copolymer, carbomers, acrylates copolymer, or acrylates $C_{10-30}$ acrylate crosspolymer; polyethoxylated urethane thickeners, or polyamide thickeners. Other suitable thickeners are based on natural polymers such as polysaccharides or polyamides and can be chemically modified. Such thickeners include for instance hydroxyethyl celluloses, hydroxypropyl celluloses, xathan gum, gelatine, agar-agar, carragenens, alginates or mixtures thereof. The thickeners are preferably used in an amount of about 0.001 to 5.0 wt.-% based on the total weight of the hair care preparation.

One or more light screening agents may be desirable in a hair care preparation according to the invention. The light screening agents are advantageously selected from UV-A, UV-B, UV-C and/or broadband filters such as in particular from the commercially available and widely used UV-filter substances octocrylene (PARSOL® 340), 4-methyl benzylidene camphor (PARSOL® 5000), ethylhexyl methoxycinnamate (PARSOL® MCX), ethylhexyl triazone (Uvinul® T-150), diethylhexyl butamido triazone (Uvasorb® HEB), 2,2'-methylene-bis-(6-(2H-benzotriazole-2-yl)-4-(1,1,3,3,-tetramethylbutyl)-phenol (Tinosorb® M), bis-ethylhexyloxyphenol methoxyphenyl triazine (Tinosorb® S), 2,2-(1,4-phenylene)bis-(1H-benzimidazol-4,6-disulfonic acid (NeoHeliopan® AP), 2-(4-Diethylamino-2-hydroxy-benzoyl)-benzoic acid hexylester (Uvinul® A plus), polysilicone-15 (PARSOL® SLX), 2-phenyl benzimidazole sulfonic acid (PARSOL® HS), ethylhexyl salicylate (PARSOL® EHS), homomethyl salicylate (PARSOL® HMS), Benzophenone-3 (Uvinul® M 40), Benzophenone-4 (Uvinul® MS 40), PEG-25 PABA, as well as mixtures thereof.

The light screening agents are generally present in the compositions according to the invention in proportions ranging from 0.001 to 5 wt.-%, preferably ranging from 0.01 to 1 wt.-%, most preferably ranging from 0.02 to 0.5 wt.-% with respect to the total weight of the composition.

Additionally other additives, such as those commonly used by those skilled in the art may be added to the hair care preparation according to the invention. The other additives used in the hair care preparations will depend upon the type of hair care preparation desired. Other additives include for example fragrances; moisturizers such as sorbitol, propane diol, butylene glycol, glycerin, hydrolyzed silk protein, or hydrolyzed wheat protein; detangling aids such as panthenol; conditioning agents such as those disclosed in U.S. Pat. No. 5,164,177 emulsifiers; antistatic aids, extracts, proteins, vitamins, dyes, tints, colorants or combinations thereof. The other additives are typically present from 0.005 to 5 wt.-%; more preferably from 0.01 to 1 wt.-% based on total weight of the hair care preparation.

Additional other additives, as well as additional surfactants, solvents, other preservatives, and thickeners, which may be suitable in the hair care compositions may be found in the International Cosmetic Ingredients Dictionary, 5th Edition, 1993, published by the CTFA in Washington D.C.

The following examples are provided to further illustrate the processes and compositions of the present invention. These examples are illustrative only and are not intended to limit the scope of the invention in any way.

In the examples the following abbreviations or trade names are employed.
BMA=n-butyl methacrylate
EA=ethyl acrylate
EMA=ethyl methacrylate
MAA=methacrylic acid
SLES=ethoxylated sodium lauryl sulphate [30 wt % in water
AMPS=ammonium persulfate
LMKT=n-dodecyl mercaptan
i-AA=i-ascorbic acid
t-BHPO=t-butylhydroperoxide [70 wt % in water]

EXAMPLE 1

Initial charge: water (90 g), SLS (1 g)
Monomer feed: BMA (50 g), EA (10 g), EMA (20 g), MAA (20 g), LMKT (0.2 g), water (43 g), SLS (1 g).

The initial charge mixture was transferred to the reaction vessel, stirred under a nitrogen atmosphere and the temperature was raised to 80° C. The monomer feed was prepared and transferred to the feed vessel. At a reactor vessel temperature of 80° C., AMPS (0.14 g in 1 g of water) was added to the reactor. After 5 minutes the monomer feed was started. The monomer feed was fed over 90 minutes. After the feed the reactor vessel was kept at 80° C. for 15 minutes.

A post reaction was conducted using t-butyl hydroperoxide (1.3 g), i-ascorbic acid (0.9 g), water (20 g) and ferrous sulphate hepta hydrate (1 cm³, 1%). The reaction mixture was neutralised to a pH 8 to 8.5. The solids content was adjusted with water to 40%. The resulting emulsion polymer had a pH of 2.5, and a viscosity of 50 mPa·s. All viscosity measurements where made at 25° C., using spindle 1 at 160 rpm.

The solubility of the acrylic emulsion polymers according to the invention in water, ethanol as well as mixtures thereof can be tested according to the US-VOC-guidelines as "VOC 80" and "VOC 55" formulation and visible assessment of the resulting solutions. Alternatively, the turbidity can be determination with a HACH 2100 N IS Turbidimeter, 115 Vac according ISO 7027 (The threshold for turbidity is at NTU≥5. (NTU<5 means visibly clear solution)).

The hair styling properties of the acrylic emulsion polymers according to the invention can be assessed by the high humidity curl retention test:

For this test, hair tresses (Kerling; Art.Nr.826 500) are cut in switches of 2 cm width. Each switch is washed twice with 0.5 mL of a cleansing shampoo (10% Sodium Laureth Sulfate/4% Sodium Chloride): 30 s foaming, 90 s rinsing with warm water. The switches are combed 5 times and dried in a climate room at 20° C. and 65% relative humidity for at least 4 hours. The weight of the switches is standardized under these conditions for 2 g+/−0.2 g for hair (without rubber coating). Afterwards the switch is dampened with 1 g water, and evenly wetted with 0.3 g of polymer solution (5 wt.-% solids in EtOH): application with syringe from root to tip and comb 5 times. Then, the switch is curled with a spiral curler of 12 mm diameter (Basler Haarkosmetik Art. 12939).

The curler with the hair is dried for 40 min at 45° C. Then, the curler is left in the climate room at 20° C./65% rel. humidity over night. The curl is removed carefully from the curler, lay at the table and the starting length $L_0$ is taken. Than, the curl is hung up at the rubber coating in the climate chamber at 20° C./90% rel. humidity, and the Length $L_t$ is taken after following times: 0 min, 15 min, 30 min, 45 min, 60 min, 90 min, 120 min, 240 min and 360 min. For each sample, three hair switches are prepared. The curl retention values are calculated as follow:

$$C.R.[\%] = \frac{L - L_t}{L - L_0} \times 100$$

L=Length of uncurled Hair (230 mm)
Lo=Length of the curl after drying at the table
Lt=Length of hanging curl in after time t

EXAMPLE 3

Solid Styling Wax

| No | Name | Amount (wt.-%) |
|---|---|---|
| 1 | Water demin. | 47.48 |
| 2 | Isoceteth-20 | 22.00 |
| 3 | PEG-7 Glyceryl Cocoate | 10.00 |
| 4 | Acrylate emulsion polymer according to the invention | 6.00 |
| 5 | Hydrogenated Polydecene | 6.00 |
| 6 | Glycerin | 4.00 |

-continued

| No | Name | Amount (wt.-%) |
|---|---|---|
| 7 | Quaternium-26 (58%) in Propylene Glycol | 2.00 |
| 8 | AMP-95 | 1.27 |
| 9 | Propylparabene | 0.20 |
| 10 | Fragrance | 1.00 |

Mix Pos. 1 and Pos. 8, and heat them up to at 60° C. Add Pos. 4 and stir until a clear solution has been formed. Dissolve Pos. 9 in Pos. 6 under heating. Add Pos. 2, 3, 5, 7 and the Glycerin solution of Pos. 9 to the polymer solution and heat the solution up to 80° C. After 10 min, cool down to 40° C., add the fragrance with stirring and fill the mass into a jar. After several hours, the solid wax is formed.

EXAMPLE 4

Fibre Styling Pomade

| No | Name | Amount (wt.-%) |
|---|---|---|
| 1 | Water | 68.18 |
| 2 | Acrylate emulsion polymer according to the invention | 4.00 |
| 3 | AMP-95 | 1.27 |
| 4 | Sorbitol 70% | 4.00 |
| 5 | PEG-90M | 0.50 |
| 6 | Methylparabene | 0.25 |
| 7 | PEG 150/Stearyl Alcohol/SMDI Copolymer (19% in water) | 2.20 |
| 8 | Lanolin | 3.00 |
| 9 | Cetyl Dimethicone | 3.00 |
| 10 | Dicaprylyl Carbonate | 7.00 |
| 11 | Propylparabene | 0.20 |
| 12 | Fragrance | 1.00 |
| 13 | Glycol Distearate | 3.00 |
| 14 | Cyclopentasiloxene & Dimethicone Crosspolymer | 2.40 |

EXAMPLE 5

Styling Cream

| No | Name | Amount (wt.-%) |
|---|---|---|
| 2 | Water | 69.40 |
| 3 | Acrylate emulsion polymer according to the invention | 5.50 |
| 4 | PEG 150/Stearyl Alcohol/SMDI Copolymer (19% in water) | 2.20 |
| 5 | Acrylic Acid/VP-Crosspolymer | 1.20 |
| 6 | AMP-95 | 1.07 |
| 7 | Fragrance | 0.35 |
| 8 | Styrene/Acrylates Copolymer (40% in water) | 0.20 |
| 9 | Silicone Quaternium-16 & Undeceth-11 & Butyloctanol & Undeceth-5 | 1.20 |
| 10 | Ethyl Panthenol | 0.25 |
| 11 | Methylisothiazolinone (10% in Propylene Glycol) | 0.10 |
| 12 | AMP-95 to adjust pH | 0.20 |
| 13 | PEG-90M | 0.10 |

EXAMPLE 6

VOC 80 Pump Spray

| No | Name | Amount (wt.-%) |
|---|---|---|
| 1 | Ethanol | 80.00 |
| 2 | Water demin. | 13.39 |
| 3 | Acrylate emulsion polymer according to the invention | 5.00 |
| 4 | AMP-95 | 1.06 |
| 5 | Octocrylene | 0.10 |
| 6 | Panthenol | 0.10 |
| 7 | PEG-12 Dimethicone | 0.15 |
| 8 | Fragrance | 0.20 |

EXAMPLE 7

VOC 55 Pump Spray

| No | Name | Amount (wt.-%) |
|---|---|---|
| 1 | Ethanol | 55.00 |
| 2 | Water demin. | 36.57 |
| 3 | Acrylate emulsion polymer according to the invention | 6.50 |
| 4 | AMP-95 | 1.38 |
| 5 | Ethylmethoxycinnamate | 0.15 |
| 6 | Panthenol | 0.10 |
| 7 | Phenyl Trimethicone | 0.15 |
| 8 | Fragrance | 0.20 |

EXAMPLE 8

Fine Modelling Sprizz

| No | Name | Amount (wt.-%) |
|---|---|---|
| 1 | Ethanol | 25.00 |
| 2 | Water demin. | 66.31 |
| 3 | Acrylate emulsion polymer according to the invention | 3.75 |
| 4 | Acrylic Acid/VP-Crosspolymer | 0.95 |
| 5 | Silicone Quaternium-16 & Undeceth-11 & Butyloctanol & Undeceth-5 | 2.20 |
| 6 | AMP-95 | 0.74 |
| 7 | Fragrance | 0.20 |
| 8 | Polisilicone-15 | 0.25 |
| 9 | AMP-95 to andjust pH | As needed |
| 10 | Ethylpanthenol | 0.20 |
| 11 | Silica & Titanium Dioxide (EU: CI 77891) & Tin Oxide (EU: CI 77861) | 0.10 |

Adjust pH with Pos. 9 to 7.7→Viscosity=2000 mPas; add water to 100%

EXAMPLE 9

Aerosol Hairspray "Strong Hold"

| No | Name | Amount (wt.-%) |
|---|---|---|
| 1 | Ethanol | 92.1 |
| 2 | AMP-95 | 1.27 |
| 3 | Acrylate emulsion polymer according to the invention | 6.00 |
| 4 | Panthenol | 0.18 |
| 5 | Isoamyl p-Methoxycinnamate | 0.09 |
| 6 | Fragrance | 0.18 |
| 7 | PEG-12 Dimethicone | 0.18 |

This solution is bottled in an appropriate can (aluminium, tinplate), crimped with an aerosol valve and propane/butane mixture is added as propellant. The pressure of the propellant, the ratio of effective solution:propellant and the actuator is chosen according to the product requirements as spray rate, spray pattern, particle size and particle size distribution. A typical composition would be: 60% Effective Solution; 40% propane/butane 2.5 bar.

The invention claimed is:

1. A cosmetic composition comprising:
   (a) an acrylic emulsion polymer which is an emulsion polymerized reaction product of a monomer mixture of raw monomer materials consisting of methacrylic acid, n-butyl methacrylate, ethyl acrylate, ethyl methacrylate, and less than 5 wt. %, based on 100 wt. % of the monomer mixture, of impurities or additives which may be present in the raw monomer materials, and
   (b) a cosmetically acceptable carrier.

2. The cosmetic composition according to claim 1, wherein the composition comprises 0.01-20 wt. %, based on total weight of the cosmetic composition, of the acrylic emulsion polymer.

3. The cosmetic composition according to claim 2, wherein the composition comprises 0.05-10 wt. % of the acrylic emulsion polymer.

4. The cosmetic composition according to claim 1, wherein the monomer mixture consists of 10-30 wt. % of methacrylic acid, 40-60 wt. % of n-butyl methacrylate, 5-15 wt. % of ethyl acrylate and 10-30 wt. % of ethyl methacrylate, and less than 5 wt. % of impurities or additives, based on 100 wt. % of the monomer mixture.

5. The cosmetic composition according to claim 1, wherein the monomer mixture consists of 17-22 wt. % of methacrylic acid, 45-56 wt. % of n-butyl methacrylate, 9-15 wt. % of ethyl acrylate and 15-25 wt. % of ethyl methacrylate, and less than 5 wt. % of impurities or additives, based on 100 wt. % of the monomer mixture.

6. The cosmetic composition according to claim 1, wherein the ethyl methacrylate (EMA) and ethyl acrylate (EA) in the monomer mixture are present in an amount to provide a coefficient of EMA to EA (w/w) in a range of 4 to 1.

7. The cosmetic composition according to claim 6, wherein the coefficient of EMA to EA (w/w) is in the range of 2 to 1.

8. The cosmetic composition according to claim 6, wherein the coefficient of EMA to EA (w/w) is in the range of about 2.0 to 1.3.

9. The cosmetic composition according to claim 1, wherein the methacrylic acid in the monomer composition is present in an amount less than 25 wt. %.

10. A hair styling preparation which comprises the cosmetic composition according to claim 1.

11. The hair styling preparation according to claim 10, wherein the hair styling preparation is in the form of a styling cream, styling gel, liquid hair-setting preparation, hair foams or hairspray.

12. The hair styling preparation according to claim 10, wherein the hair styling preparation is an aerosol hairspray.

13. The hair styling preparation according to claim 10, which further comprises at least one additional hair fixative resin.

14. A hair styling polymer which comprises an acrylic emulsion polymer which is an emulsion polymerization reaction product of a monomer mixture consisting of methacrylic acid, n-butyl methacrylate, ethyl acrylate and ethyl methacrylate, and less than 5 wt. % of impurities or additives, based on 100 wt. % of the monomer mixture.

* * * * *